United States Patent

Behl et al.

[19]

[11] Patent Number: 5,874,450

[45] Date of Patent: Feb. 23, 1999

[54] INTRANASAL FORMULATIONS FOR PROMOTING SLEEP AND METHOD OF USING THE SAME

[75] Inventors: Charanjit R. Behl, Hauppauge; Jorge C. DeMeireles, Syosset; Harish K. Pimplaskar, Lindenhurst; Vincent D. Romeo, Massapequa Park; Anthony P. Sileno, Brookhaven Hamlet; Wei J. Xia, Melville, all of N.Y.

[73] Assignee: Nastech Pharmaceutical Company, Inc., Hauppauge, N.Y.

[21] Appl. No.: 939,279

[22] Filed: Sep. 29, 1997

Related U.S. Application Data

[60] Provisional application No. 60/026,811, Sep. 27, 1996.

[51] Int. Cl.$^6$ ............................. A61K 9/08; A61K 31/435
[52] U.S. Cl. .............................................. 514/357; 514/923
[58] Field of Search ................................................ 514/357

[56] References Cited

U.S. PATENT DOCUMENTS

| | | | |
|---|---|---|---|
| 4,053,628 | 10/1977 | Stevenson et al. | 424/283 |
| 4,364,945 | 12/1982 | Whittle | 424/247 |
| 4,603,131 | 7/1986 | Bernstein et al. | 514/220 |
| 4,624,965 | 11/1986 | Wenig | 514/619 |
| 4,729,997 | 3/1988 | Wenig | 514/225 |
| 4,749,700 | 6/1988 | Wenig | 514/225.2 |
| 4,822,823 | 4/1989 | Yamamoto et al. | 514/690 |
| 5,116,847 | 5/1992 | Gilbert et al. | 514/327 |
| 5,215,739 | 6/1993 | Kamishita et al. | 424/45 |
| 5,419,898 | 5/1995 | Ikejiri et al. | 424/78.04 |

OTHER PUBLICATIONS

Pharmaceutical Research—PDD 7485—"Development of a Doxylamine Succinate Nasal Solution and its Comparison With Oral Doxylamine Succinate Product", Sep. 1995 (Supplement) vol. 12, No. 9.

*Primary Examiner*—Shep K. Rose
*Attorney, Agent, or Firm*—Hoffmann & Baron, LLP

[57] ABSTRACT

Intranasal dosage units for promoting sleep in a mammal are disclosed. The dosage units are in the form of an aqueous buffered solution having a pH greater than 7.0, a sleep-promoting amount of Doxylamine, and an effective amount of an anionic surfactant. The anionic surfactant amount is an amount effective to provide a peak plasma concentration of Doxylamine to be reached within 30 minutes of administering the dosage unit to the nasal mucosa of a mammal. The dosage units are particularly suitable for administration to humans.

30 Claims, 14 Drawing Sheets

INTRANASAL FORMULATIONS FOR PROMOTING SLEEP AND METHOD OF USING THE SAME

This application is a continuation-in-part of Provisional Application No. 60/026,811 filed Sep. 27, 1996, now abandoned.

FIELD OF THE INVENTION

The present invention relates to pharmaceutical formulations that promote sleep upon administration to the nasal mucosa of a mammal, and more particularly to pharmaceutical formulations containing Doxylamine that promote sleep upon administration to the nasal mucosa.

BACKGROUND OF THE INVENTION

Doxylamine, and more particularly Doxylamine Succinate, has been widely used throughout the years to promote sleep in humans. Typically, Doxylamine Succinate is administered orally in tablet form at dosages ranging from 12.5 to 25 milligrams (mg).

However, two disadvantages have become evident with the oral administration of Doxylamine. First, oral administration provides the subject with a slow onset of sleepiness due to its pharmokinetic profile. Thus, the time frame for sleep to be achieved is usually 45 to 60 minutes after oral administration.

A second disadvantage with oral administration is that a peak blood plasma concentration of Doxylamine is not reached until usually 90 minutes from administration. This continued to rise in plasma levels after the onset of sleep is additionally exacerbated by a slow gradual reduction in plasma levels. Thus, the subject upon awakening after a typical eight hours of sleep still has relatively high plasma levels of Doxylamine. The result of these two characteristics of oral administration is the common occurrence of grogginess associated with orally administered Doxylamine.

Suitable alternatives to oral administration include, inter alia, nasal delivery. In fact, U.S. Pat. No. 4,749,700 to Wenig teaches intranasal formulations for delivering systemic amounts of antihistamines, including Doxylamine Succinate, to a mammal. However, while this patent teaches intranasal formulations containing Doxylamine Succinate, these formulations have been found to exhibit a pharmokinetic profile that mimics oral administration.

Accordingly there is a need in the art for pharmaceutical formulations containing Doxylamine, and more particularly Doxylamine Succinate, that provide a shorter onset of sleep-promoting Doxylamine plasma levels as compared to oral administration.

In addition, there is a need in the art for sleep-promoting pharmaceutical formulations of Doxylamine that do not exhibit continually increasing plasma levels once sleep has been induced, therefore, minimizing grogginess associated with Doxylamine administration.

It is, therefore, an object of the present invention to provide Doxylamine pharmaceutical formulations that promote sleep, while providing the subject with a faster onset of sleep-promoting plasma levels of the drug as compared to oral administration. It is also an object of the present invention to provide Doxylamine pharmaceutical formulations that do not exhibit continually increasing plasma levels once sleep has been induced.

SUMMARY OF THE INVENTION

The present invention is a pharmaceutical dosage unit for promoting sleep in a mammal by intranasal administration. The intranasal dosage unit contains an aqueous buffered solution having a pH greater than 7.0, a sleep-promoting amount of Doxylamine and 0.1 to 5.0 weight percent (wt. %) of an anionic surfactant. Preferably, the dosage unit has a pH of at least 7.5 with a pH of at least 8.0 being more preferred. The sleep promoting amount of Doxylamine can range from 2 to 50 milligrams (mg) with 5 to 25 mg being preferred, and 10 to 20 mg being more preferred. Doxylamine is preferably provided as Doxylamine Succinate.

The anionic surfactant amount can be as low as 0.1 wt. %, with at least 0.25 wt. % being preferable, with at least 0.5 wt. % being more preferred, and with at least 1.0 wt. % being even more preferred. The anionic surfactant can be a salt of a long chain hydrocarbon with a functional group that can include, but not limited to, carboxylates, sulfonates and sulfates. Salts of long chain hydrocarbons with sulfate functional groups are preferred with sodium lauryl sulfate being more preferred.

The present invention also includes a method of using the above-described dosage unit to promote sleep in a mammal. This is accomplished by administering to the nasal mucosa of the mammal a dosage unit containing an aqueous buffered solution having a pH greater than 7.0, a sleep-promoting amount of Doxylamine and 0.1 to 5 wt. % of the anionic surfactant. The dosage units of the present invention have been found to be particularly suitable for promoting sleep in humans.

Advantageously, the dosage units of the present invention provide a rapid onset of peak blood plasma levels of Doxylamine after being administered to the nasal mucosa of the mammal. Through the use of the dosage units of the present invention, peak plasma concentrations of Doxylamine can be achieved within thirty minutes of administration, more preferably within twenty minutes of administration, and even more preferably within ten minutes of administration. In addition, the dosage units of the present invention upon administration to the nasal mucosa exhibit a decrease in blood plasma levels of Doxylamine after reaching peak plasma concentrations. This advantageously facilitates decreased plasma levels in the mammal after a sufficient amount of sleep thereby minimizing grogginess upon awakening.

DETAILED DESCRIPTION OF THE INVENTION

Figure 1:
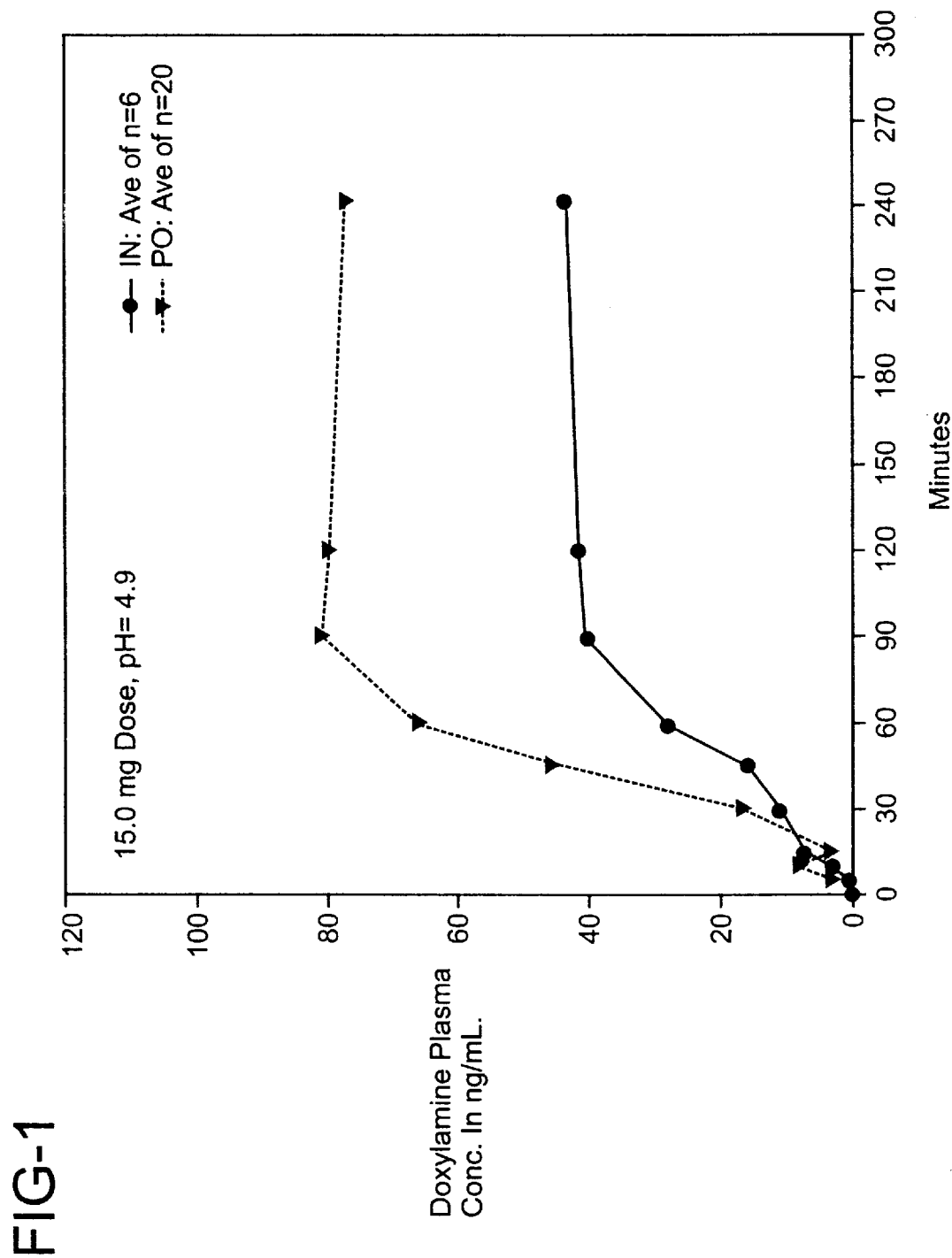
FIG. 1 is a plot graph of Doxylamine blood plasma concentrations in humans as a function of time for a 15.0 mg dose of Doxylamine Succinate nasal spray having a pH of 4.9, versus a 25 mg oral dose.

In accordance with the present invention, pharmaceutical formulations containing Doxylamine have been developed for promoting sleep in a mammal upon administration to the nasal mucosa of the mammal. It has unexpectedly been found that a dosage unit of an aqueous solution of a sleep-promoting amount of Doxylamine, more particularly Doxylamine Succinate, with a combination of a pH greater than 7.0 and an effective amount of an anionic surfactant advantageously provides a peak blood plasma concentration within thirty minutes of administration to the nasal mucosa of the mammal.

The rapid onset of a peak plasma concentration of Doxylamine provides a distinct advantage over the pharmokinetic profile of orally administered Doxylamine, in which peak plasma concentrations are not usually achieved until 75 to 90 minutes after administration. In addition, it has been found that the peak plasma concentrations provided by the intranasal dosage units of the present invention are substantially equivalent quantitatively to the peak plasma concentrations exhibited by similar doses of orally administered Doxylamine. The phrase "substantially equivalent" means that the peak plasma concentration provided by an intranasal dosage unit of the present invention is approximately ±20%, preferably ±15%, and more preferably ±10%, of the peak plasma concentration provided by an equivalent oral dosage.

In accordance with the present invention, one of ordinary skill in the art can adjust the pH of the dosage unit and the amount of the an anionic surfactant to provide a peak plasma concentration of Doxylamine within at least thirty minutes of administration to the nasal mucosa. Preferably, the pH and the anionic surfactant amount is adjusted to a level that provides a peak plasma concentration within twenty minutes, more preferably within ten minutes, and even more preferably within 7.5 minutes, of administering the dosage unit to the nasal mucosa of the mammal.

As a result of providing peak plasma concentrations within 30 minutes of administration to the nasal mucosa, the dosage units advantageously provide reduced Doxylamine plasma concentrations once a peak plasma concentration has been achieved as compared to oral dosing. As known in the art, orally administered Doxylamine after reaching a peak plasma concentration exhibits a "plateau effect" in which plasma levels slowly decrease with the passage of time. Thus, the subject (i.e., mammal) upon awakening after a sufficient amount of sleep, e.g., 8 hours, still exhibits high levels of Doxylamine. The dosage units of the present invention do not exhibit this plateau effect, which in turn facilitates a reduced level of Doxylamine in the blood stream upon awakening of the mammal thereby minimizing the unwanted side effect of grogginess commonly associated with oral Doxylamine.

As previously described, the intranasal dosage units of the present invention have a pH greater than 7.0. Preferably, the pH of the intranasal dosage units should be at least 7.5, with a pH of at least 8.0 being more preferred. Although the pH values greater than 10 can be utilized in accordance with the present invention, a pH greater than 10 may cause irritation to the nasal mucosa.

The alkaline pH of the dosage unit (i.e., a pH greater than 7.0) is provided by using a pharmaceutically acceptable buffer system. Examples of buffer systems to be utilized include, but are not limited to, acetate, citrate, carbonate and phosphate buffers, with a carbonate buffer being preferred.

Pharmaceutically acceptable alkalizers can also be utilized with the buffer system to adjust the pH of the dosage unit. Examples of pharmaceutically acceptable alkalizers that can be utilized in conjunction with the buffer system include, but are not limited to, edetol, potassium carbonate, potassium hydroxide, sodium borate, sodium carbonate, sodium hydroxide and trolamine (triethanolamine). One particularly preferred alkalizer is trolamine.

The anionic surfactant is provided in the amount effective for a peak plasma concentration of Doxylamine to be achieved within thirty minutes of administering the dosage unit to the nasal mucosa of the mammal. Stated otherwise, an effective amount of the anionic surfactant is an amount that will allow the dosage unit having a pH greater than 7.0 to exhibit a peak plasma concentration of Doxylamine within thirty minutes of administration to the nasal mucosa. The anionic surfactant should be provided in amount between 0.1 to 5 wt. % of the solution. Preferably, the anionic surfactant is provided in a concentration of at least 0.25 wt. %, with at least 0.5 wt. % being more preferable, and at least 1.0 wt. % being more preferred. However, the exact concentration will be dependent on the pH of the dosage unit, which can be easily ascertained by a skilled artisan.

The anionic surfactant can be any pharmaceutically acceptable anionic surfactant. Examples of suitable anionic surfactants to be utilized include, but are not limited to, salts of long chain hydrocarbons having one or more of the following functional groups: carboxylates; sulfonates; and sulfates. Salts of long chain hydrocarbons having sulfate functional groups are preferred, such as sodium cetostearyl sulfate, sodium dodecyl sulfate and sodium tetradecyl sulfate. One particularly preferred anionic surfactant is sodium lauryl sulfate (i.e., sodium dodecyl sulfate). By reference to a long chain hydrocarbon, references made to hydrocarbon chains from 6 to 30 carbons, with 10 to 20 carbons being preferred.

In accordance with the invention, the dosage units contain a sleep-promoting amount of Doxylamine. Doxylamine is preferably provided as Doxylamine Succinate, although other salts forms or derivatives of Doxylamine can be utilized.

As will be apparent to those skilled in the art, the exact amount required to promote sleep in a mammal will of course depend on the variety of factors, including the weight and age of the mammal. In addition, because the onset of sleep with oral Doxylamine occurs prior to the peak plasma levels being achieved, intranasal dosages of Doxylamine due to the improved pharmokinetic profile can advantageously provide sleep-promoting plasma levels at lower dosages. For example, a 25 mg oral dose of Doxylamine Succinate will normally promote sleep in a mammal within 45 to 60 minutes of administration at a blood plasma level ranging from 45 to 65 nanograms/milliliter (ng/ml). A peak plasma level of about 80 ng/ml is eventually achieved at about 90 minutes. However, through the present invention, intranasal dosage units with less than 25 mg Doxylamine Succinate can achieve 45 to 65 ng/ml plasma levels as the peak plasma level within 30 minutes or less. Thus, less Doxylamine can be utilized with the pharmaceutical dosage units of the invention while providing sleep-promotion equivalent to higher doses given orally.

The sleep-promoting amounts of Doxylamine can range from 2 to 50 milligrams (mg) per dose, with 5 to 25 mg being preferred and 10 to 20 mg being more preferred. Typically, 12.5 mg or 25 mg dosages are orally administered to promote sleep. Thus, if desired, the dosages provided by the dosage units of the present invention can be the less than, the same as, or greater than oral dosages.

The dosage units of the present invention can range from 0.1 to 0.4 ml per dose. Thus, for example, to provide a 25 mg dose with a 0.1 ml dosage unit, a Doxylamine concentration of 25 mg per 0.1 ml is required. However, if a dosage unit of 0.4 ml is utilized, a Doxylamine concentration of 6.25 mg per 0.1 ml is required. The actual concentration necessary for a desired effect can easily be ascertained by one of ordinary skill in the art.

The dosage units of the present invention can be provided in any pharmaceutically acceptable form suitable for administration to the nasal mucosa. Examples of forms in which the dosage units of the present invention can be provided include, but are not limited to, nasal sprays, nasal gels, nasal drops or as a nasal ointment. A nasal spray is preferred since it will facilitate the rapid onset of peak plasma concentration of Doxylamine.

In an alternative embodiment of the invention, the pharmaceutical formulations can be dehydrated to form a powder dosage unit, which can be administered to the nasal mucosa. The powder dosage units can be administered neat, or in conjunction with a pharmaceutically acceptable carrier. In one particularly preferred alternative embodiment, the powder formulation is incorporated into a microparticulate often referred to as microspheres or nanospheres. Processes for incorporating pharmaceuticals into such microparticulates are well known in the art.

The dosage units of the present invention can also include other additives such as humectants and preservatives. A humectant or soothening agent is utilized to inhibit drying of the nasal mucosa and to prevent irritation. Any pharmaceutical acceptable humectant can be utilized, in which examples include, but are not limited to, sorbitol, propylene glycol and glycerol. The amounts utilized will vary with the agent selected and can be easily determined by one of ordinary skill in the art.

A pharmaceutically acceptable preservative is also employed to increase the shelf life of the composition. Any pharmaceutically acceptable preservative can be utilized with examples, including, but are not limited to, thimerosal, chlorobutanol, benzyl alcohol, parabens, and benzalkonium chloride. Preferably, benzalkonium chloride is utilized. The concentration of the preservative will range from 0.2 to 2 wt. %, although the actual concentration will vary with the preservative selected.

The dosage units may also be isotonic, although isotonicity is not required. Typically, pharmaceutically acceptable agents such as dextrose, boric acid, sodium tartarate, propylene glycol and other inorganic or organic solutes can be utilized to adjust tonicity. Sodium chloride is particularly preferred if a buffer system containing sodium is utilized.

The present invention also includes a method of promoting sleep in the mammal by administrating to the nasal mucosa of the mammal the above described intranasal dosage units. As illustrated by the following examples, intranasal dosage units are particularly suitable for administration to the nasal mucosa of humans.

The following non-limiting examples also illustrate the advantageous use of intranasal Doxylamine Succinate formulations prepared in accordance with the present invention as compared to orally administered Doxylamine Succinate and intranasal Doxylamine Succinate formulations prepared following the teachings of U.S. Pat. No. 4,749,700.

EXAMPLES

Example 1

A Doxylamine Succinate formulation was prepared utilizing conventional techniques with the components set forth in Table 1 to provide a 15.0 mg/0.1 ml intranasal dosage unit having a pH of 4.9, as taught in U.S. Pat. No. 4,749,700.

TABLE 1

| Dosage Unit: 15.0 mg Doxylamine Succinate/0.1 ml | |
|---|---|
| Ingredients: | Quantity: grams/100 ml |
| Doxylamine Succinate, USP | 15.0 |
| Sodium Citrate Dihydrate, USP | 0.512 |
| Citric Acid Anhydrous, USP | 0.192 |
| Benzalkonium Chloride (50%), NF | 0.04 |
| Edetate Disodium, USP | 0.01 |
| Purified Water, USP, q.s. | 100.0 ml |
| pH = 4.9 | |

The intranasal dosage units were administered to the nasal mucosa of 6 human volunteers. As a control, 25 mg of Doxylamine Succinate in tablet form were orally administered to 20 human volunteers. Blood samples were taken at various time intervals following administration. The plasma concentrations of Doxylamine in the samples taken were ascertained by High Pressure Liquid Chromatography (HPLC) following conventional techniques. The results from HPLC analysis of intranasal Doxylamine as compared to oral Doxylamine are shown in FIG. 1.

From FIG. 1, it is readily apparent that the intranasal dosage units did not provide any advantage over oral Doxylamine. In fact, the intranasal dosage units provided a slower onset of Doxylamine than achieved via oral administration.

Example 2

A Doxylamine Succinate formulation was prepared with the components set forth in Table 2 to provide a 25.0 mg/0.1 ml intranasal dosage unit having a pH of 4.9, as taught in U.S. Pat. No. 4,749,700.

TABLE 2

Dosage Unit: 25.0 mg Doxylamine Succinate/0.1 ml

| Ingredients: | Quantity: grams/100 ml |
| --- | --- |
| Doxylamine Succinate, USP | 25.0 |
| Sodium Citrate Dihydrate, USP | 0.512 |
| Citric Acid Anhydrous, USP | 0.192 |
| Benzalkonium Chloride (50%), NF | 0.04 |
| Edetate Disodium, USP | 0.01 |
| Purified Water, USP, q.s. | 100.0 ml |
| pH = 5.0 | |

As in Example 1, the intranasal dosage units were administered to the nasal mucosa of 6 human volunteers. Blood samples were taken at various time intervals and the plasma concentration of Doxylamine in these samples were ascertained by HPLC analysis. The results from HPLC analysis of intranasal Doxylamine as compared to oral Doxylamine are shown in FIG. 2.

Figure 2:
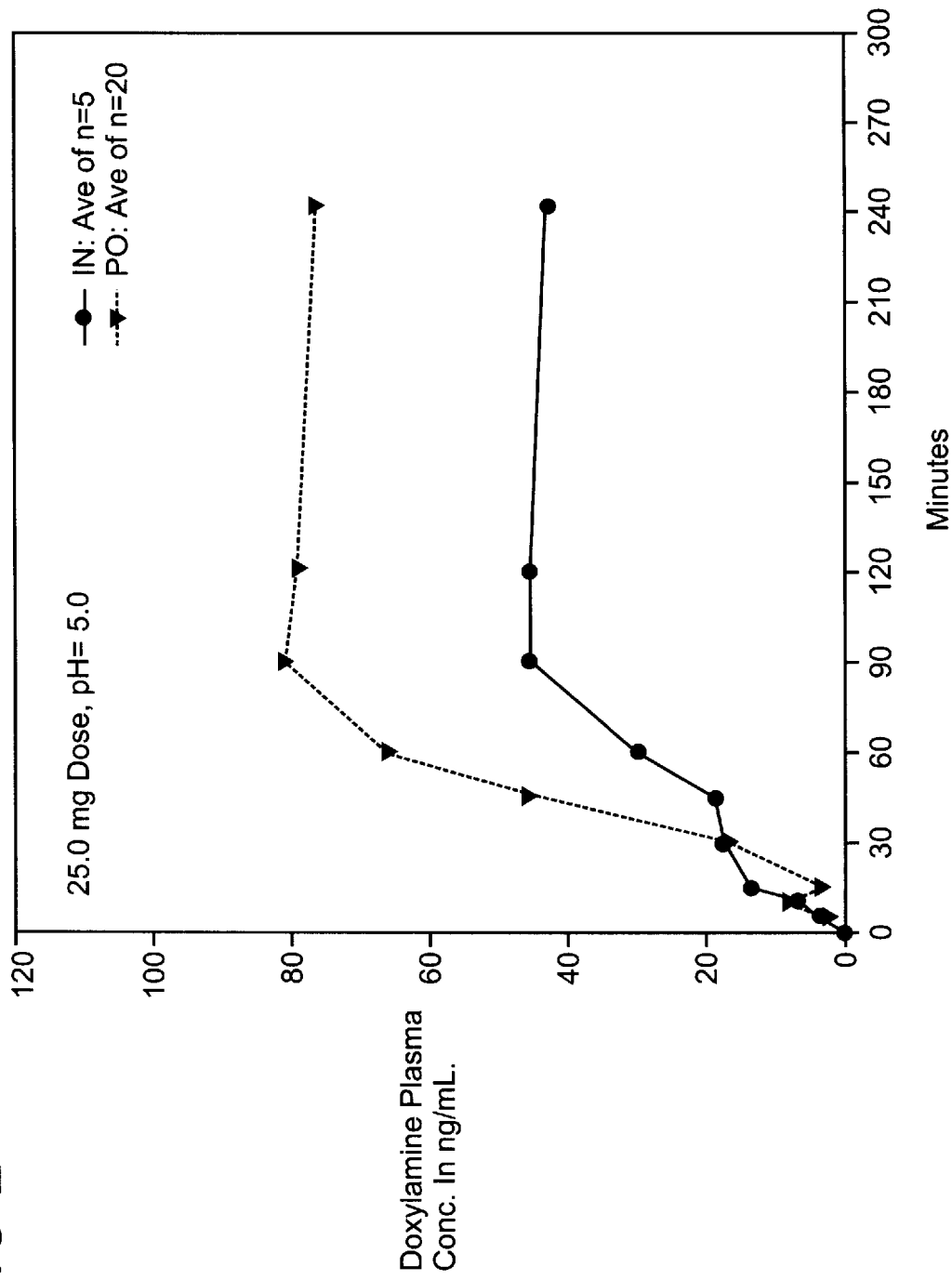
FIG. 2 is a plot graph of Doxylamine blood plasma concentrations in humans as a function of time for a 25.0 mg dose of Doxylamine Succinate nasal spray having a pH of 5.0, versus a 25 mg oral dose.

FIG. 2 shows that intranasal Doxylamine exhibited only a slightly higher plasma level than oral Doxylamine within the first 30 minutes. At 30 minutes from administration, both delivery routes exhibited virtually the same plasma levels. After 90 minutes from administration, both delivery routes reached peak plasma concentrations. Surprisingly, however, the 25 mg dose given intranasally only provided a peak plasma concentration approximately one-half of the peak plasma concentration provided by the 25 mg oral dose.

Example 3

A Doxylamine Succinate gel formulation was prepared with the components set forth in Table 3 to provide a 25.0 mg/0.1 ml intranasal dosage unit having a pH of 4.9, as taught in U.S. Pat. No. 4,749,700.

TABLE 3

Dosage Unit: 25.0 mg Doxylamine Succinate/0.1 ml

| Ingredients: | Quantity: grams/100 ml |
| --- | --- |
| Doxylamine Succinate, USP | 25.0 |
| Sodium Citrate, Dihydrate, USP | 0.51 |
| Citric Acid Anhydrous, USP | 0.19 |
| Hydroxypropylcellulose, NF (gelling agent) | 2.0 |
| Edetate Disodium, USP | 1.0 |
| Benzalkonium Chloride (50%), NF | 0.04 |
| Purified Water, USP, q.s. | 100.0 ml |
| pH = 4.9 | |

The intranasal dosage units were administered to the nasal mucosa of 5 human volunteers. Blood samples were taken at various time intervals and the plasma concentration of Doxylamine in these samples were ascertained by HPLC analysis. The results from HPLC analysis of intranasal Doxylamine as compared to oral Doxylamine are shown in FIG. 3.

Figure 3:
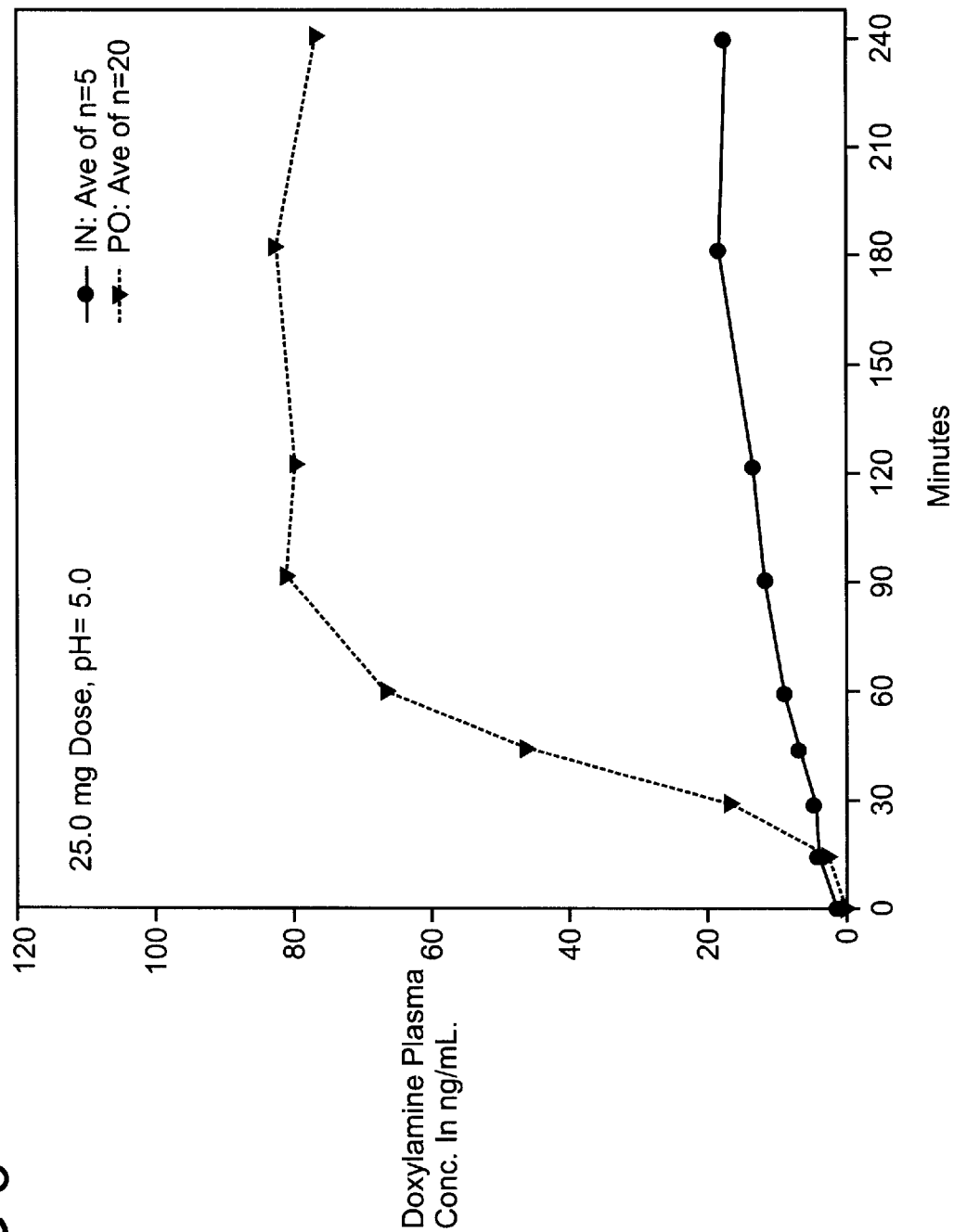
FIG. 3 is a plot graph of Doxylamine blood plasma concentrations in humans as a function of time for a 25.0 mg dose of Doxylamine Succinate nasal gel having a pH of 5.0, versus a 25 mg oral dose.

FIG. 3 shows that the intranasal gel dosage units provided no advantage over orally administered Doxylamine. Unlike the nasal spray in Example 2, the gel did not provide a higher plasma concentration than oral Doxylamine within the first 30 minutes. Moreover, the peak plasma level achieved by the intranasal gel was significantly less than that provided by the nasal spray in Example 2.

Example 4

A Doxylamine Succinate gel formulation was prepared with the components set forth in Table 4 to provide a 25.0 mg/0.1 ml intranasal dosage unit having a pH of 4.9 and 5.0 wt. % of a nonionic surfactant, Tween 80, as taught in U.S. Pat. No. 4,749,700.

TABLE 4

Dosage Unit: 25.0 mg Doxylamine Succinate/0.1 ml

| Ingredients: | Quantity: grams/100 ml |
| --- | --- |
| Doxylamine Succinate, USP | 25.0 |
| Sodium Citrate Dihydrate, USP | 0.51 |
| Citric Acid Anhydrous, USP | 0.19 |
| Polysorbate 80, USP (Tween 80) | 5.0 |
| Hydroxypropylcellulose, NF | 2.0 |
| Benzalkonium Chloride (50%), NF | 0.04 |
| Purified Water, USP, q.s. | 100.0 ml |
| pH = 5.0 | |

The intranasal dosage units were administered to the nasal mucosa of 5 human volunteers. Blood samples were taken at various time intervals and the plasma concentration of Doxylamine in these samples were ascertained by HPLC analysis. The results from HPLC analysis of intranasal Doxylamine as compared to oral Doxylamine are shown in FIG. 4.

Figure 4:
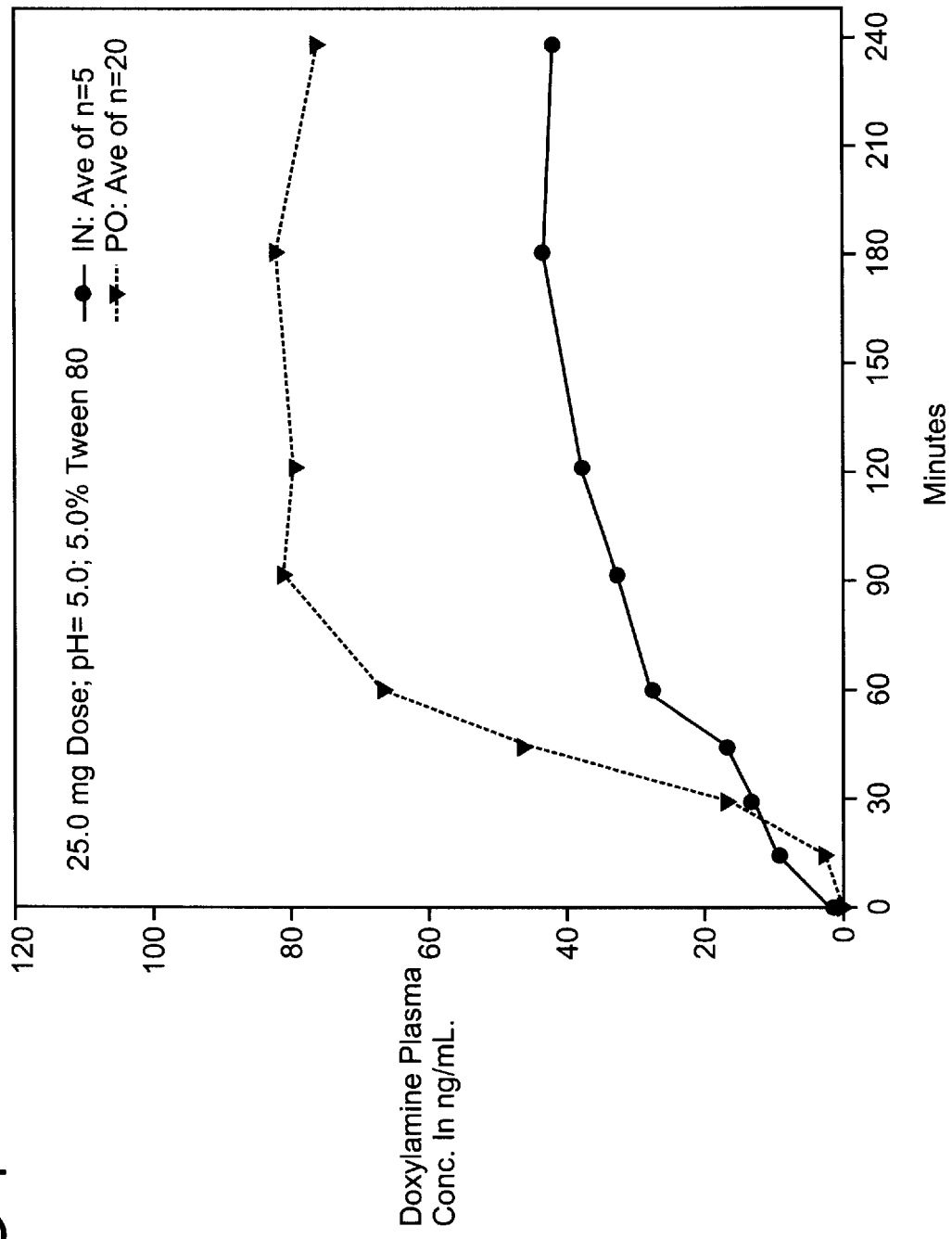
FIG. 4 is a plot graph of Doxylamine blood plasma concentrations in humans as a function of time for a 25.0 mg dose of Doxylamine Succinate nasal gel having a pH of 5.0 and 5 wt. % of a nonionic surfactant, versus a 25 mg oral dose.

FIG. 4 shows that the addition of the nonionic surfactant Tween 80 to the intranasal gel formulation did not significantly alter the pharmokinetic profile of the gel. The intranasal dosage units provided only a slight higher plasma level within 30 minutes from administration as compared to oral Doxylamine. However, after 30 minutes from administration, oral Doxylamine still provided significantly greater plasma concentrations.

Example 5

A Doxylamine Succinate formulation was prepared with the components set forth in Table 5 to provide a 25.0 mg/0.1 ml intranasal dosage unit having a pH of 4.9 and 1.0 wt. % of an anionic surfactant, sodium lauryl sulfate.

TABLE 5

Dosage Unit: 25.0 mg Doxylamine Succinate/0.1 ml

| Ingredients: | Quantity: grams/100 ml |
| --- | --- |
| Doxylamine Succinate, USP | 25.0 |
| Sodium Citrate Dihydrate, USP | 0.51 |
| Citric Acid Anhydrous, USP | 0.19 |
| Sodium Lauryl Sulfate, NF | 1.0 |
| Hydroxypropylcellulose, NF | 2.0 |

TABLE 5-continued

Dosage Unit: 25.0 mg Doxylamine Succinate/0.1 ml

| Ingredients: | Quantity: grams/100 ml |
| --- | --- |
| Benzalkonium Chloride (50%), NF | 0.04 |
| Purified Water, USP, q.s. | 100.0 ml |
| pH = 5.0 | |

The intranasal dosage units were administered to the nasal mucosa of 5 human volunteers. Blood samples were taken at various time intervals and the plasma concentration of Doxylamine in these samples were ascertained by HPLC analysis. The results from HPLC analysis of intranasal Doxylamine as compared to oral Doxylamine are shown in FIG. 5.

Figure 5:
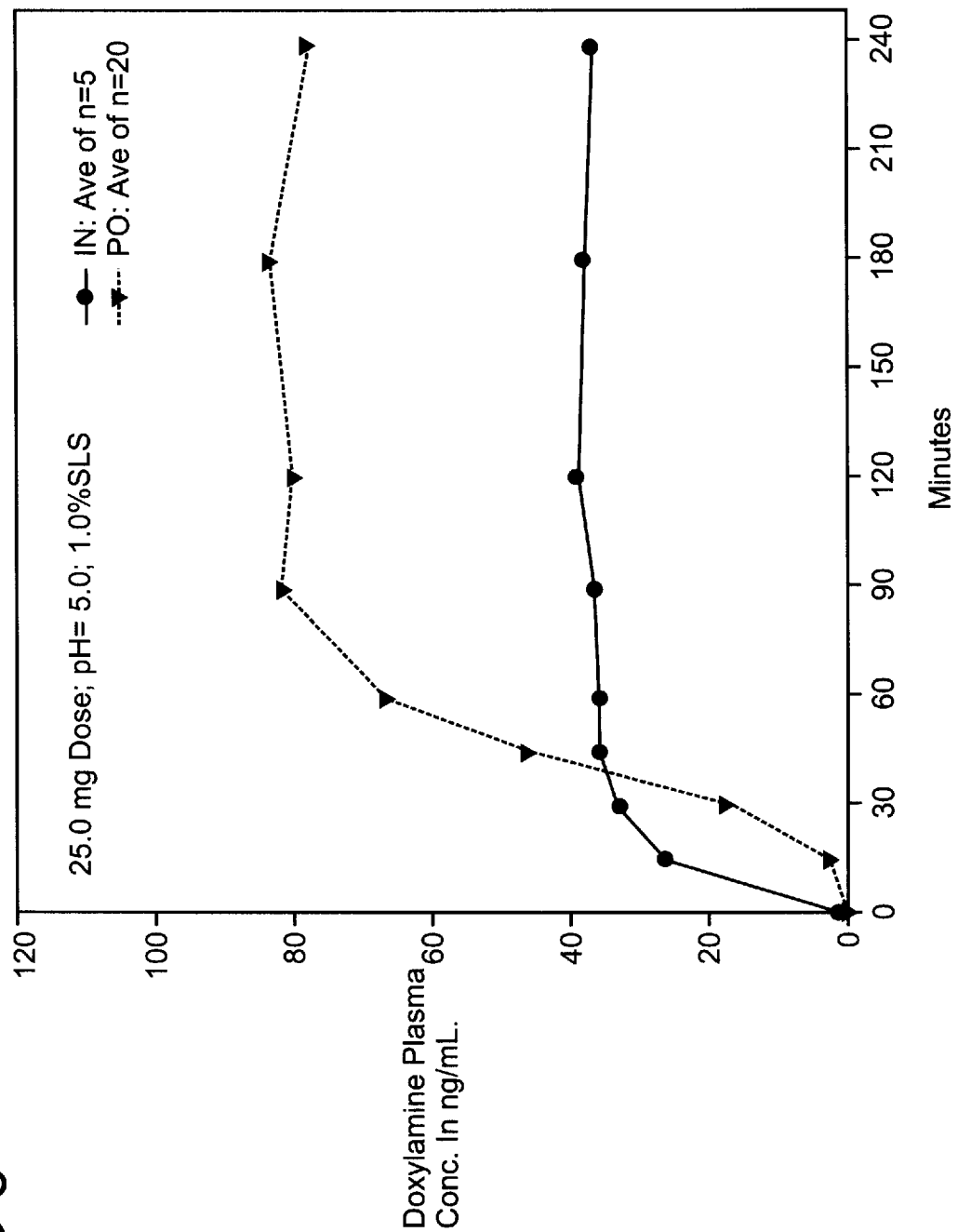
FIG. 5 is a plot graph of Doxylamine blood plasma concentrations in humans as a function of time for a 25.0 mg dose of Doxylamine Succinate nasal gel having a pH of 5.0 and 1 wt. % of an anionic surfactant, versus a 25 mg oral dose.

FIG. 5 shows that the addition of the anionic surfactant to the intranasal formulation provided a faster onset of Doxylamine than achieved by oral Doxylamine. However, FIG. 5 also shows that the anionic surfactant still did not remedy the substantially lower peak plasma concentration exhibited by intranasal Doxylamine as compared to oral Doxylamine. Overall, these intranasal dosage units provided a pharmokinetic profile substantially similar to the pharmokinetic profile of oral Doxylamine, especially evident by the similar plateau effect once peak plasma concentrations were achieved.

Example 6

A Doxylamine Succinate formulation was prepared with the components set forth in Table 6 to provide a 12.5 mg/0.1 ml intranasal dosage unit having a pH of 7.1, as taught in U.S. Pat. No. 4,749,700.

TABLE 6

Dosage Unit: 12.5 mg Doxylamine Succinate/0.1 ml

| Ingredients: | Quantity: grams/100 ml |
| --- | --- |
| Doxylamine Succinate, USP | 12.5 |
| Sodium Phosphate, Dibasic, USP | 2.71 |
| Citric Acid Anhydrous, USP | 0.09 |
| Edetate Disodium, USP | 0.01 |
| Benzalkonium Chloride (50%), NF | 0.04 |
| Sodium Hydroxide, NF | to adjust pH |
| Purified Water, USP, q.s. | 100.0 ml |
| pH = 7.1 | |

The intranasal dosage units were administered to the nasal mucosa of 5 human volunteers. Blood samples were taken at various time intervals and the plasma concentration of Doxylamine in these samples were ascertained by HPLC analysis. The results from HPLC analysis of intranasal Doxylamine as compared to oral Doxylamine are shown in FIG. 6.

Figure 6:
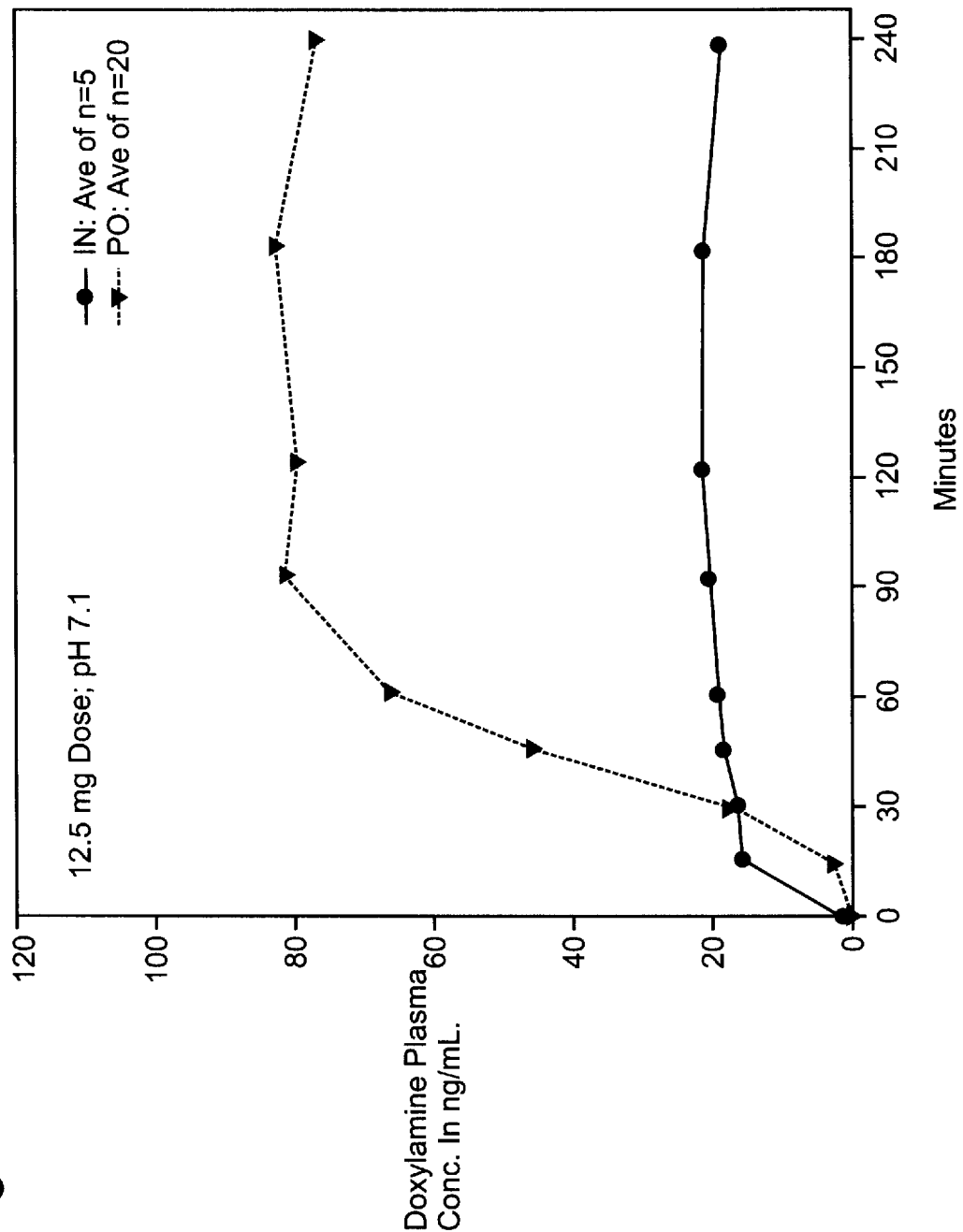
FIG. 6 is a plot graph of Doxylamine blood plasma concentrations in humans as a function of time for a 12.5 mg dose of Doxylamine Succinate nasal spray having a pH of 7.1, versus a 25 mg oral dose.

FIG. 6 shows that the intranasal dosage units at a pH of 7.1 exhibited a faster onset of Doxylamine within 30 minutes of administration than achieved by oral Doxylamine. However, the overall pharmokinetic profile exhibited by the intranasal dosage units still mimicked oral Doxylamine.

Example 7

A Doxylamine Succinate formulation was prepared with the components set forth in Table 7 to provide a 12.5 mg/0.1 ml intranasal dosage unit having a pH of 7.3 and 0.25 wt. % of an anionic surfactant, sodium lauryl sulfate.

TABLE 7

Dosage Unit: 12.5 mg Doxylamine Succinate/0.1 ml

| Ingredients: | Quantity: grams/100 ml |
| --- | --- |
| Doxylamine Succinate, USP | 12.5 |
| Sodium Phosphate Dibasic, USP | 2.71 |
| Citric Acid Anhydrous, USP | 0.09 |
| Sodium Lauryl Sulfate, NF | 0.25 |
| Glycerin 96%, USP | 10.0 |
| Benzalkonium Chloride (50%), NF | 0.04 |
| Sodium Hydroxide, NF | to adjust pH |
| Purified Water, USP, q.s. | 100.00 ml |
| pH = 7.3 | |

The intranasal dosage units were administered to the nasal mucosa of 5 human volunteers. Blood samples were taken at various time intervals and the plasma concentration of Doxylamine in these samples were ascertained by HPLC analysis. The results from HPLC analysis of intranasal Doxylamine as compared to oral Doxylamine are shown in FIG. 7.

Figure 7:
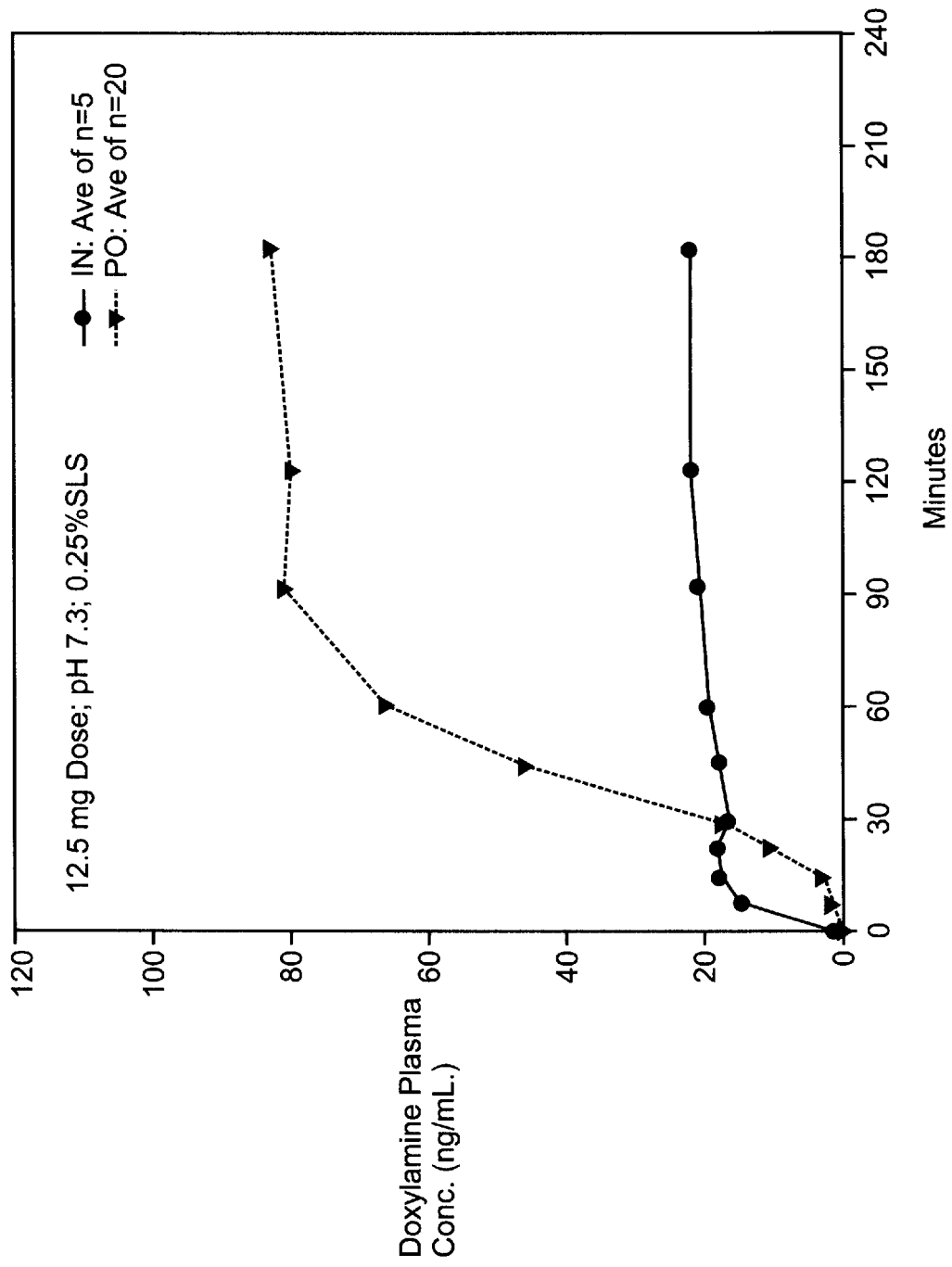
FIG. 7 is a plot graph of Doxylamine blood plasma concentrations in humans as a function of time for a 12.5 mg dose of Doxylamine Succinate nasal spray having a pH of 7.3 and 0.25 wt. % of an anionic surfactant, versus a 25 mg oral dose.

FIG. 7 shows that the intranasal dosage units at a pH of 7.3 and 0.25 wt. % of sodium lauryl sulfate (SLS) provided essentially the same pharmokinectic profile as the intranasal dosage units in Example 6. Thus, the addition of 0.25 wt. % SLS did not appear to provide any advantage.

Example 8

A Doxylamine Succinate formulation was prepared with the components set forth in Table 8 to provide a 12.5 mg/0.1 ml intranasal dosage unit having a pH of 7.3 and 0.5 wt. % of the anionic surfactant, sodium lauryl sulfate.

TABLE 8

Dosage Unit: 12.5 mg Doxylamine Succinate/0.1 ml

| Ingredients: | Quantity: grams/100 ml |
| --- | --- |
| Doxylamine Succinate, USP | 12.5 |
| Sodium Phosphate Dibasic, USP | 2.71 |
| Citric Acid Anhydrous, USP | 0.09 |
| Sodium Lauryl Sulfate, NF | 0.50 |
| Glycerin 96%, USP | 10.0 |
| Benzalkonium Chloride (50%), NF | 0.04 |
| Sodium Hydroxide, NF | to adjust pH |
| Purified Water, USP, q.s. | 100.00 ml |
| pH = 7.3 | |

The intranasal dosage units were administered to the nasal mucosa of 5 human volunteers. Blood samples were taken at various time intervals and the plasma concentration of Doxylamine in these samples were ascertained by HPLC analysis. The results from HPLC analysis of intranasal Doxylamine as compared to oral Doxylamine are shown in FIG. 8.

Figure 8:
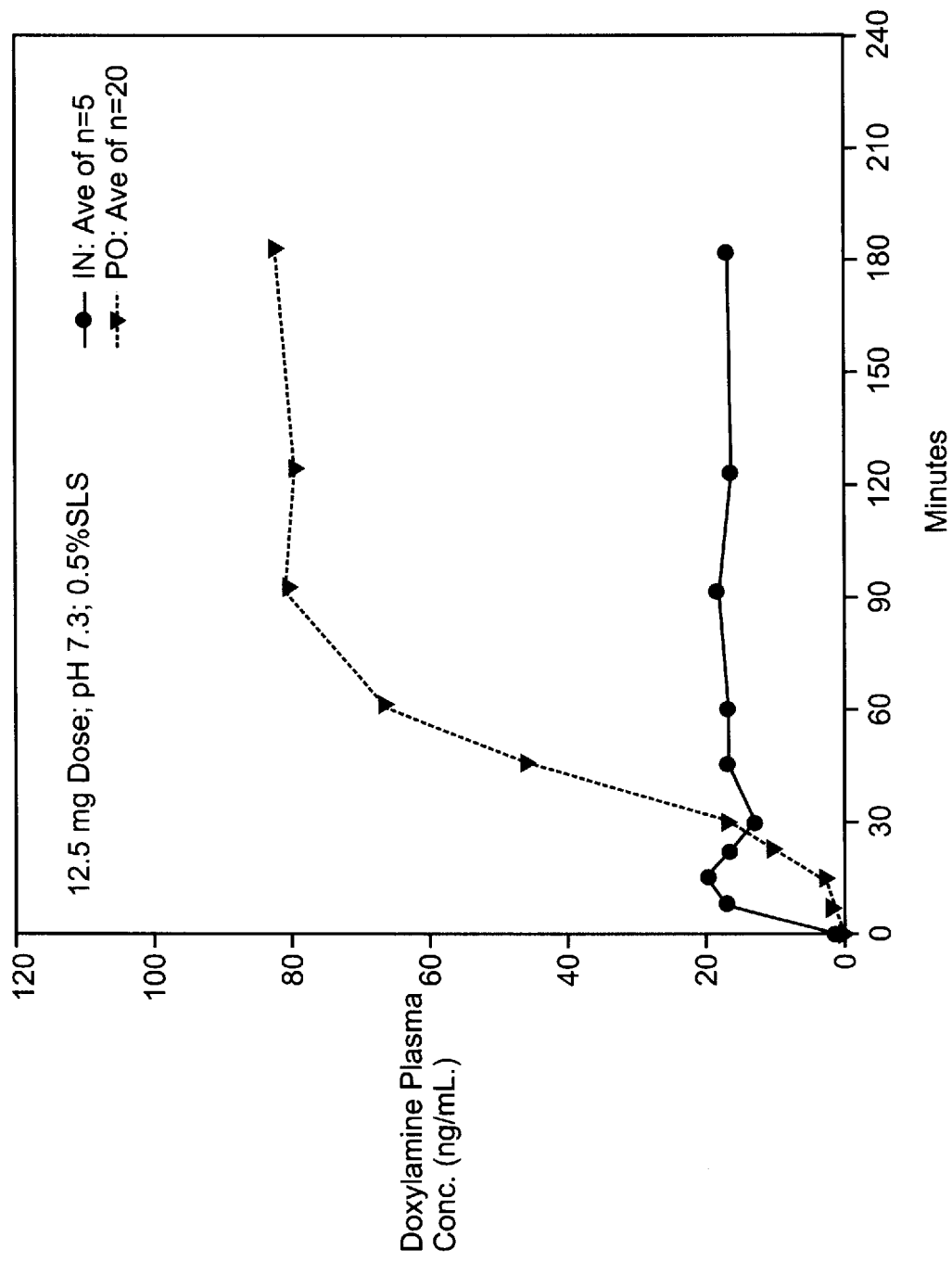
FIG. 8 is a plot graph of Doxylamine blood plasma concentrations in humans as a function of time for a 12.5 mg dose of Doxylamine Succinate nasal spray having a pH of 7.3 and 0.5 wt. % of an anionic surfactant, versus a 25 mg oral dose.

FIG. 8 shows that the intranasal dosage units at a pH of 7.3 and 0.5 wt. % SLS exhibited substantially the same pharmokinetic profile as the intranasal dosage units of Examples 6 and 7. Thus, the addition of 0.5 wt. % SLS did not appear to provide any advantage.

Example 9

A Doxylamine Succinate formulation was prepared with the components set forth in Table 9 to provide a 12.5 mg/0.1 ml intranasal dosage unit having a pH of 7.3 and 1.0 wt. % of the anionic surfactant, sodium lauryl sulfate.

TABLE 9

Dosage Unit: 12.5 mg Doxylamine Succinate/0.1 ml

| Ingredients: | Quantity: grams/100 ml |
| --- | --- |
| Doxylamine Succinate, USP | 12.5 |
| Sodium Phosphate Dibasic, USP | 2.71 |
| Citric Acid Anhydrous, USP | 0.09 |
| Sodium Lauryl Sulfate, NF | 1.0 |
| Glycerin 96%, USP | 10.0 |
| Benzalkonium Chloride (50%), NF | 0.04 |
| Sodium Hydroxide, NF | to adjust pH |
| Purified Water, USP, q.s. | 100.00ml |
| pH = 7.3 | |

The intranasal dosage units were administered to the nasal mucosa of 5 human volunteers. Blood samples were taken at various time intervals and the plasma concentration of Doxylamine in these samples were ascertained by HPLC analysis. The results from HPLC analysis of intranasal Doxylamine as compared to oral Doxylamine are shown in FIG. 9.

Figure 9:
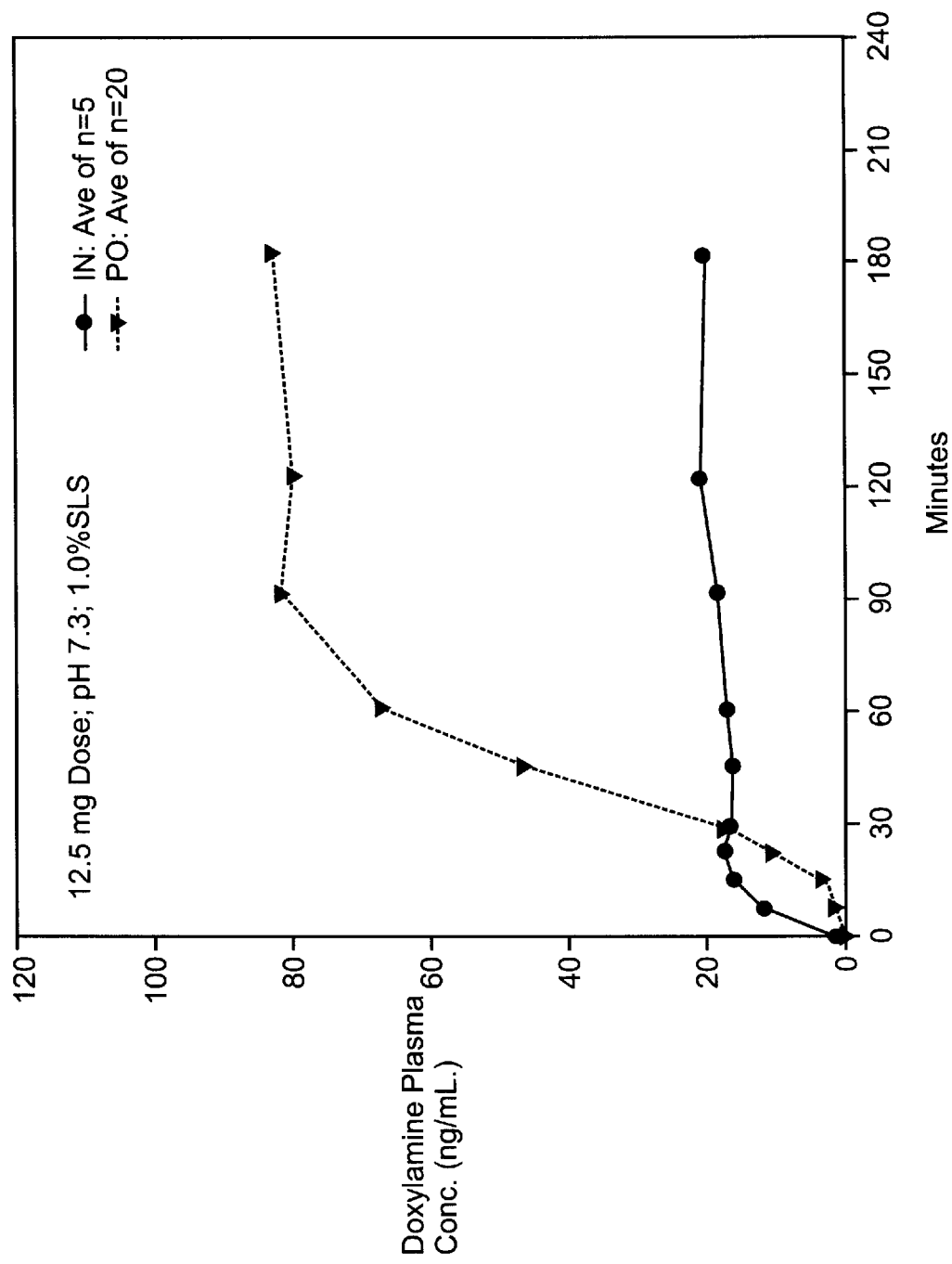
FIG. 9 is a plot graph of Doxylamine blood plasma concentrations in humans as a function of time for a 12.5 mg dose of Doxylamine Succinate nasal spray having a pH of 7.3 and 1 wt. % of an anionic surfactant, versus a 25 mg oral dose.

FIG. 9 shows that the intranasal dosage units at a pH of 7.3 and 1.0 wt. % SLS exhibited substantially the same pharmokinetic profile as the intranasal dosage units of Examples 6, 7 and 8. Thus, the addition of 1.0 wt. % SLS did not appear to provide any advantage.

Example 10

A Doxylamine Succinate formulation was prepared with the components set forth in Table 10 to provide a 12.5 mg/0.1 ml intranasal dosage unit having a pH of 8.0±0.5 and 1.7 wt. % of the cationic surfactant/alkalizer, trolamine.

TABLE 10

Dosage Unit: 12.5 mg Doxylamine Succinate/0.1 ml

| Ingredients: | Quantity: grams/100 ml |
| --- | --- |
| Doxylamine Succinate, USP | 12.5 |
| Citric Acid, USP | 0.09 |
| Sodium Phosphate Dibasic, USP | 2.71 |
| Glycerin 96%, USP | 10.0 |
| Trolamine, NF | to adjust pH |
| Sodium Hydroxide, NF | to adjust pH |
| Benzalkonium Chloride (50%), NF | 0.04 |
| Purified Water, USP, q.s. | 100.00ml |
| pH = 8.0 ± 0.5 | |

The intranasal dosage units were administered to the nasal mucosa of 5 human volunteers. Blood samples were taken at various time intervals and the plasma concentration of Doxylamine in these samples were ascertained by HPLC analysis. The results from HPLC analysis of intranasal Doxylamine as compared to oral Doxylamine are shown in FIG. 10.

Figure 10:
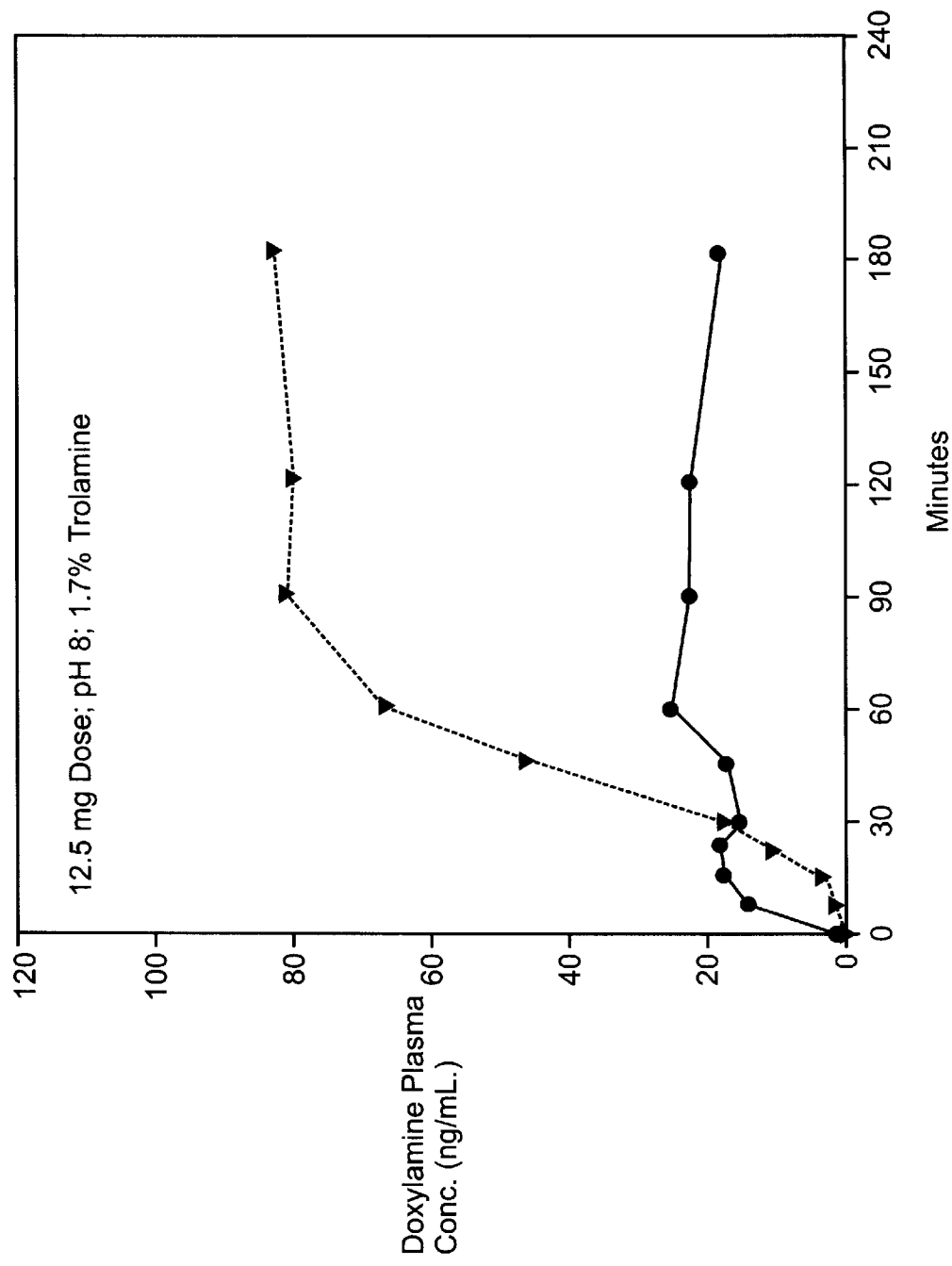
FIG. 10 is a plot graph of Doxylamine blood plasma concentrations in humans as a function of time for a 12.5 mg dose of Doxylamine Succinate nasal spray having a pH of 8.0±0.5 and 1.7 wt. % of a cationic surfactant/alkalizer, versus a 25 mg oral dose.

FIG. 10 shows that the intranasal dosage units at a pH of 8.0±0.5 and 1.7 wt. % of the cationic surfactant/alkalizer, trolamine, exhibited substantially the same pharmokinetic profile as the intranasal dosage units of Examples 6, 7, 8 and 9. Thus, the addition of 1.7 wt. % trolamine did not appear to provide any advantage.

Example 11

A Doxylamine Succinate formulation was prepared with the components set forth in Table 11 to provide a 25.0 mg/0.1 ml intranasal dosage unit having a pH of 8.1 with no cationic surfactant/alkalizer, trolamine.

TABLE 11

Dosage Unit: 25.0 mg Doxylamine Succinate/0.1 ml

| Ingredients: | Quantity: grams/100 ml |
| --- | --- |
| Doxylamine Succinate, USP | 25.0 |
| Sodium Carbonate, N.F | 5.0 |
| Sodium Bicarbonate, USP | 0.11 |
| Glycerin 96%, USP | 10.0 |
| Benzalkonium Chloride (50%), NF | 0.04 |
| Purified Water, USP, q.s. | 100.00ml |
| pH = 8.1 | |

The intranasal dosage units were administered to the nasal mucosa of 5 human volunteers. Blood samples were taken at various time intervals and the plasma concentration of Doxylamine in these samples were ascertained by HPLC analysis. The results from HPLC analysis of intranasal Doxylamine as compared to oral Doxylamine are shown in FIG. 11.

Figure 11:
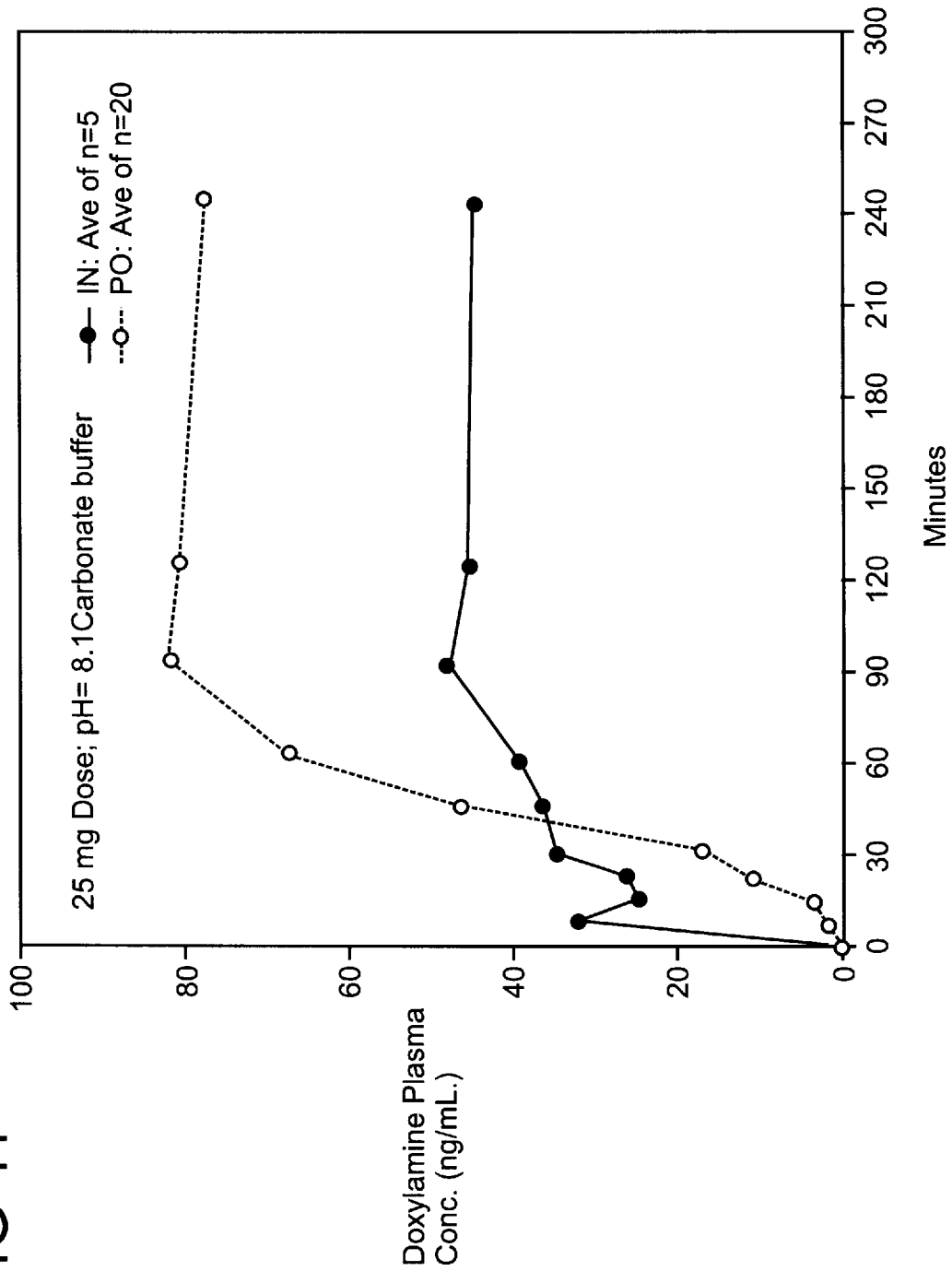
FIG. 11 is a plot graph of Doxylamine blood plasma concentrations in humans as a function of time for a 12.5 mg dose of Doxylamine Succinate nasal spray having a pH of 8.1, versus a 25 mg oral dose.

FIG. 11 shows that the intranasal dosage units at a pH of 8.1 with no cationic surfactant/alkalizer, trolamine, exhibited substantially the same pharmokinetic profile as the intranasal dosage units of Examples 6, 7, 8, 9 and 10, with only a slightly higher plasma concentration of Doxylamine.

Example 12

A Doxylamine Succinate formulation was prepared with the components set forth in Table 12 to provide a 25.0 mg/0.1 ml intranasal dosage unit having a pH of 8.0±0.5 with 1.0 wt. % of the anionic surfactant, sodium lauryl sulfate.

TABLE 12

Dosage Unit: 25.0 mg Doxylamine Succinate/0.1 ml

| Ingredients: | Quantity: grams/100 ml |
| --- | --- |
| Doxylamine Succinate, USP | 25.0 |
| Sodium Phosphate Dibasic, USP | 2.71 |
| Citric Acid Anhydrous, USP | 0.09 |
| Sodium Lauryl Sulfate, NF | 1.0 |
| Glycerin 96%, USP | 10.0 |
| Oleic Acid, USP | 0.5 |
| Benzalkonium Chloride (50%), NF | 0.04 |
| Sodium Hydroxide, NF | to adjust pH |
| Trolamine, NF | to adjust pH |
| Purified Water, USP, q.s. | 100.00ml |
| pH = 8.0 ± 0.5 | |

The intranasal dosage units were administered to the nasal mucosa of 5 human volunteers. Blood samples were taken at various time intervals and the plasma concentration of Doxylamine in these samples were ascertained by HPLC analysis. The results from HPLC analysis of intranasal Doxylamine as compared to oral Doxylamine are shown in FIG. 12.

Figure 12:
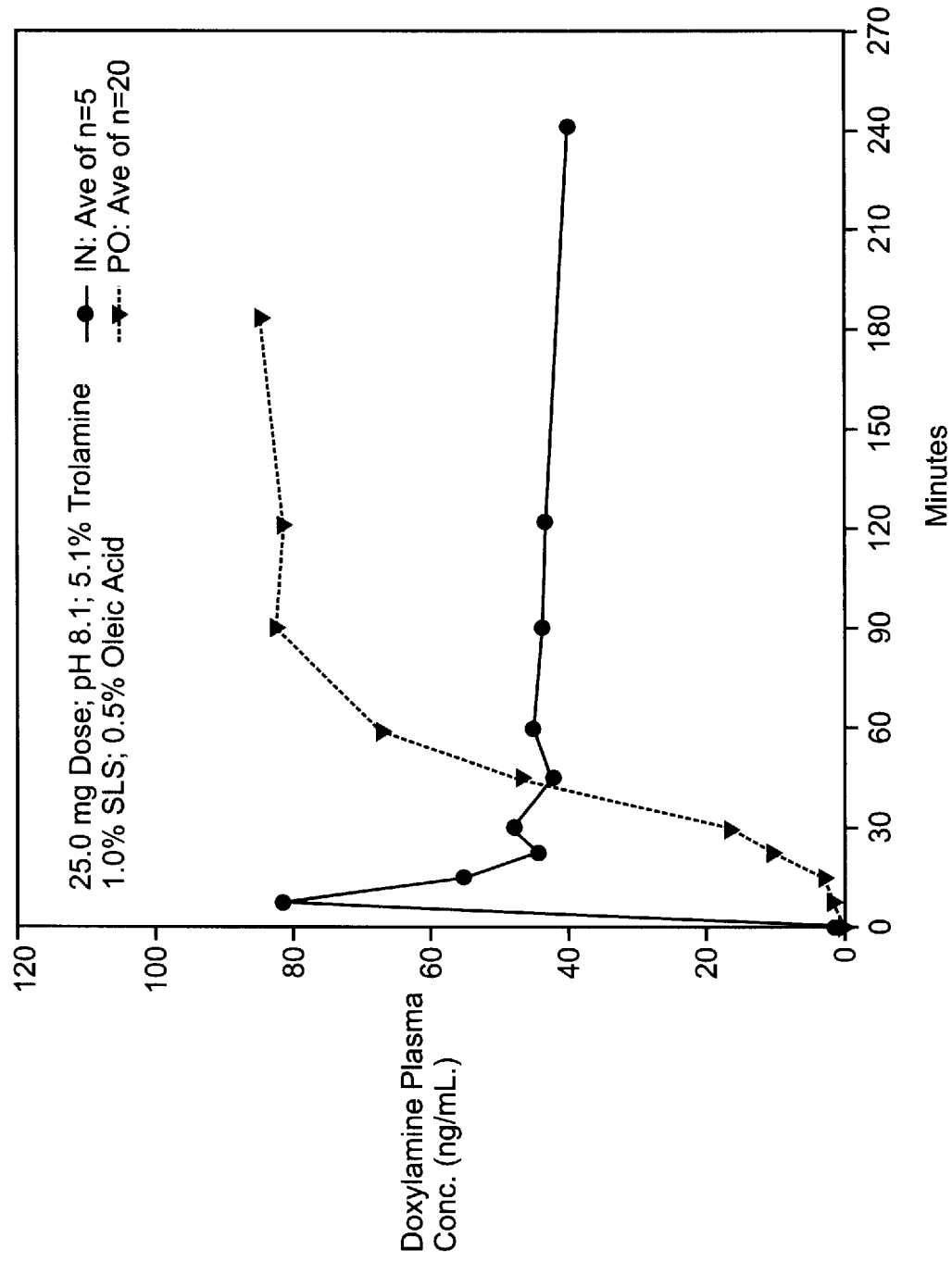
FIG. 12 is a plot graph of Doxylamine blood plasma concentrations in humans as a function of time for a 25.0 mg dose of Doxylamine Succinate nasal spray having a pH of 8.2 and 1 wt. % of an anionic surfactant, versus a 25 mg oral dose.

From FIG. 12, it is readily apparent that the addition of 1.0 wt. % SLS dramatically altered the pharmokinetic profile exhibited by the intranasal dosage units at a pH of 8.0±0.5. As seen in FIG. 12, the intranasal dosage units unexpectedly exhibited an average peak plasma concentration of about 80 ng/ml within 30 minutes of administration. More surprisingly, the intranasal dosage units exhibited a peak plasma concentration within 7.5 minutes of administration, which was quantitatively equivalent to the peak plasma concentration exhibited by oral Doxylamine at 90 minutes from administration. This was contrary to the pharmokinetic profiles exhibited by the intranasal dosage units of Examples 1–11, which at best provided only peak plasma concentrations that were one-half of those provided by the same doses given orally.

In addition to the rapid onset of a peak plasma concentration equivalent oral Doxylamine, the intranasal dosage units exhibited a significant decrease in plasma levels once the peak plasma concentration was reached (i.e., plasma levels did not plateau out). This was contrary to the pharmokinetic profile observed for oral Doxylamine and for intranasal dosage units of Examples 1–11, which exhibited a plateau effect once peak plasma concentrations had been reached. Thus, the addition of the anionic surfactant, sodium lauryl sulfate, to the intranasal formulation inverted the pharmokinetic profile exhibited by oral Doxylamine and the intranasal formulations of the Examples 1–11. Such a reversal in the pharmokinetic profile was totally unexpected.

Example 13

A Doxylamine Succinate formulation was prepared with the components set forth in Table 13 to provide a 25.0 mg/0.1 ml intranasal dosage unit having a pH of 8.16 with 1.0 wt. % of the anionic surfactant, sodium lauryl sulfate.

TABLE 13

Dosage Unit: 25.0 mg Doxylamine Succinate/0.1 ml

| Ingredients: | Quantity: grams/100 ml |
| --- | --- |
| Doxylamine Succinate, USP | 25.0 |
| Sodium Phosphate Dibasic, USP | 2.71 |
| Citric Acid Anhydrous, USP | 0.09 |
| Sodium Lauryl Sulfate, NF | 1.0 |
| Glycerin 96%, USP | 10.0 |
| Benzalkonium Chloride (50%), NF | 0.04 |
| Sodium Hydroxide, NF | 2.5 |
| Trolamine, NF | 4.6 |
| Purified Water, USP, q.s. | 100.00ml |
| pH = 8.16 | |

The intranasal dosage units were administered to the nasal mucosa of 5 human volunteers. Blood samples were taken at various time intervals and the plasma concentration of Doxylamine in these samples were ascertained by HPLC analysis. The results from HPLC analysis of intranasal Doxylamine as compared to oral Doxylamine are shown in FIG. 13.

Figure 13:
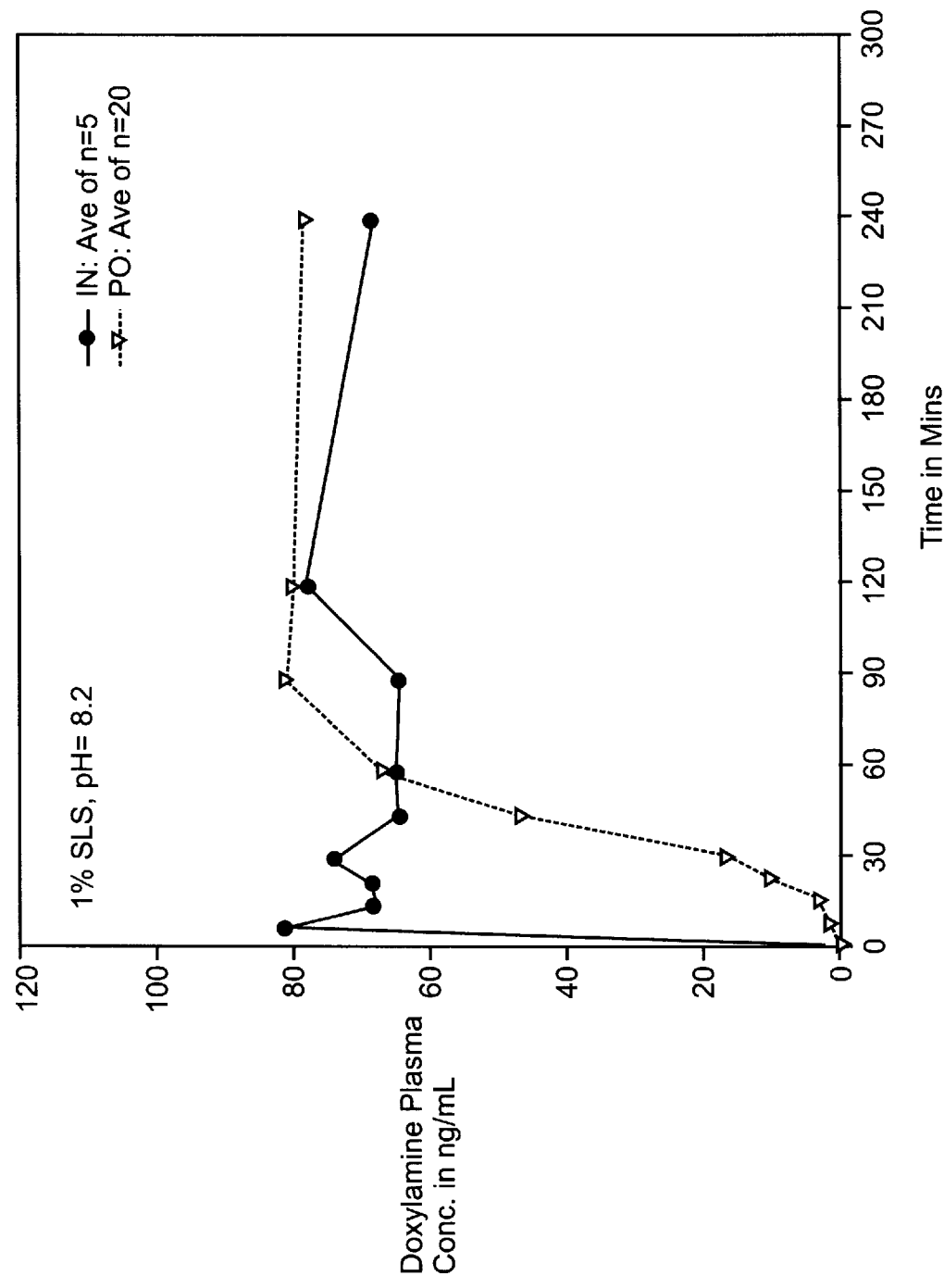
FIG. 13 is a plot graph of Doxylamine blood plasma concentrations in humans as a function of time for a 25.0 mg dose of Doxylamine Succinate nasal spray having a pH of 8.2 and 1 wt. % of an anionic surfactant, versus a 25 mg oral dose.

From FIG. 13, it is readily apparent that the intranasal dosage units exhibited a pharmokinetic profile dramatically different from oral Doxylamine. A peak plasma concentration of about 80 ng/ml was reached within 7.5 minutes as compared 90 minutes with oral Doxylamine. As in Example 12, once a peak plasma concentration was reached, the plasma concentrations decreased rather than plateau out as observed with oral Doxylamine and the intranasal formulation of Examples 1–11.

Example 14

A Doxylamine Succinate formulation was prepared with the components set forth in Table 14 to provide a 25.0 mg/0.1 ml intranasal dosage unit having a pH of 8.17 with 1.0 wt. % of the anionic surfactant, sodium lauryl sulfate, and without the cationic surfactant/alkalizer, trolamine.

TABLE 14

Dosage Unit: 25.0 mg Doxylamine Succinate/0.1 ml

| Ingredients: | Quantity: grams/100 ml |
| --- | --- |
| Doxylamine Succinate, USP | 25.0 |
| Sodium Carbonate, NF | 4.8 |
| Sodium Bicarbonate, USP | 0.11 |
| Sodium Lauryl Sulfate, NF | 1.0 |
| Glycerin 96%, USP | 10.0 |
| Benzalkonium Chloride (50%), NF | 0.04 |
| Purified Water, USP, q.s. | 100.00ml |
| pH = 8.17 | |

The intranasal dosage units were administered to the nasal mucosa of 5 human volunteers. Blood samples were taken at various time intervals and the plasma concentration of Doxylamine in these samples were ascertained by HPLC analysis. The results from HPLC analysis of intranasal Doxylamine as compared to oral Doxylamine are shown in FIG. 14.

Figure 14:
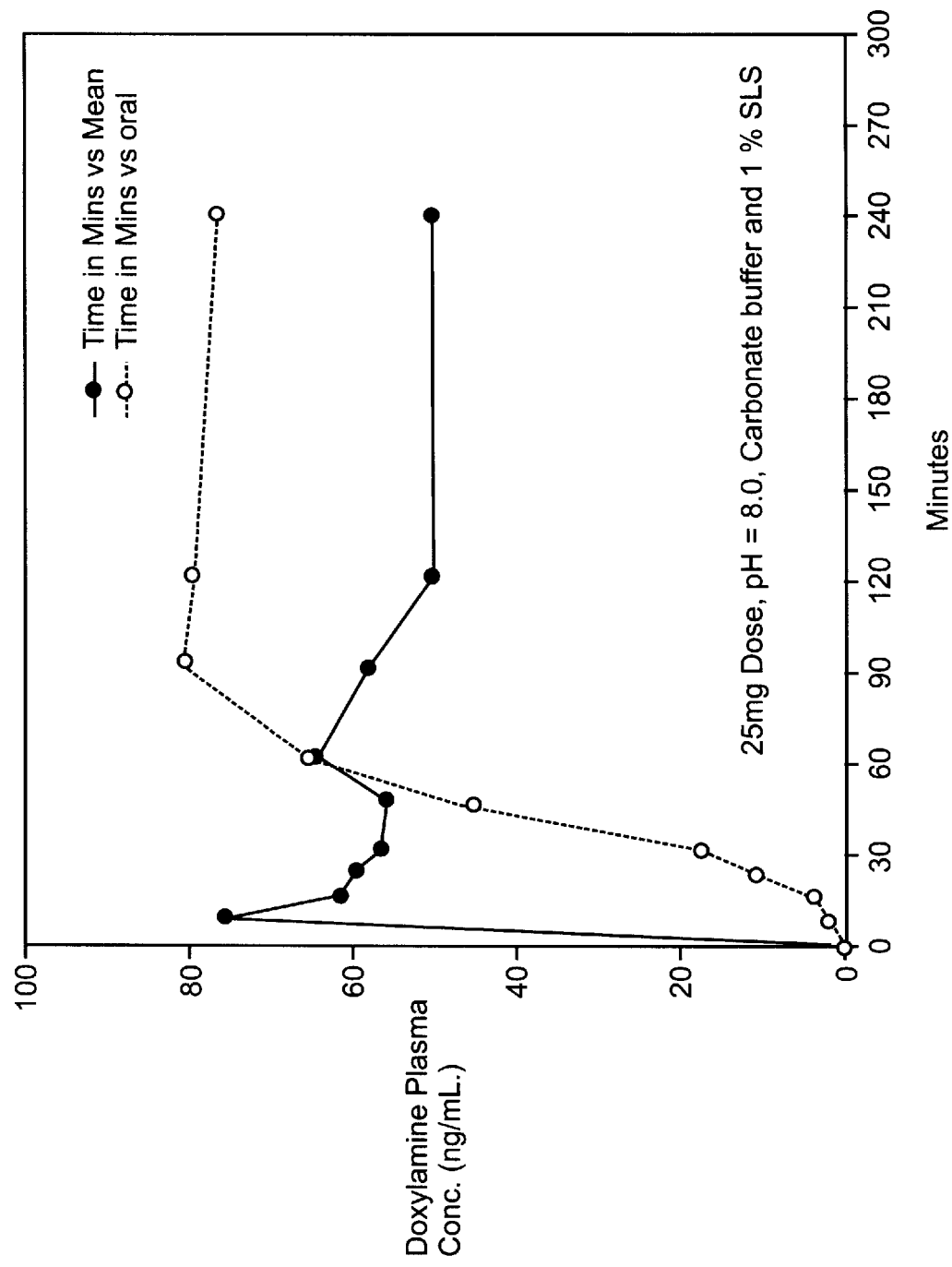
FIG. 14 is a plot graph of Doxylamine blood plasma concentrations in humans as a function of time for a 25.0 mg dose of Doxylamine Succinate nasal spray having a pH of 8.0±0.5 and 1 wt. % of an anionic surfactant, versus a 25 mg oral dose.

From FIG. 14, it can be seen that the omission of the cationic surfactant/alkalizer, trolamine, did not affect the altered pharmokinetic profile exhibited by the intranasal dosage units prepared in accordance with the invention. Thus, the absence of trolamine illustrates that the altered pharmokinetic profile can only be attributed to the combination of an alkaline pH and the use of an effective amount of an anionic surfactant.

While the invention has been described as to what are presently believed to be the preferred embodiments of the invention, those skilled in the art will realize the various changes and modifications which can be made to the invention without departing from the spirit of such invention. All such changes and modifications will fall within the scope of the present invention and are therefore intended to be claimed.

We claim:

1. An intranasal dosage unit for promoting sleep in a mammal, comprising:
   an aqueous buffered solution having a pH greater than 7.5, a sleep-promoting amount of doxylamine and 0.1 to 5.0 wt. % of an anionic surfactant.

2. An intranasal dosage unit as claimed in claim 1, wherein said pH is at least 8.0.

3. An intranasal dosage unit as claimed in claim 1, wherein said sleep-promoting amount of doxylamine is from 2 to 50 milligrams.

4. An intranasal dosage unit as claimed in claim 3, wherein said sleep-promoting amount of doxylamine is from 5 to 25 milligrams.

5. An intranasal dosage unit as claimed in claim 4, wherein said sleep-promoting amount of doxylamine is from 10 to 20 milligrams.

6. An intranasal dosage unit as claimed in claim 1, wherein said anionic surfactant is at least 0.25 wt. %.

7. An intranasal dosage unit as claimed in claim 6, wherein said anionic surfactant is at least 0.5 wt. %.

8. An intranasal dosage unit as claimed in claim 7, wherein said anionic surfactant amount is at least 1.0 wt. %.

9. An intranasal dosage unit as claimed in claim 1, wherein said anionic surfactant is a salt of a long chain hydrocarbon with a functional group selected from the group consisting of carboxylates, sulfonates and mixtures thereof.

10. An intranasal dosage unit as claimed in claim 1, wherein said anionic surfactant is a salt of a long chain hydrocarbon with sulfate functional group.

11. An intranasal dosage unit as claimed in claim 10, wherein said anionic surfactant is sodium lauryl sulfate.

12. A method of promoting sleep in a mammal, which comprises:

administering to the nasal mucosa of said mammal a dosage unit comprising an aqueous buffered solution having a pH greater than 7.5, a sleep-promoting amount of doxylamine and 0.1 to 5.0 wt. % of an anionic surfactant.

13. A method as claimed in claim 12, wherein said pH is at least 8.0.

14. A method as claimed in claim 12, wherein said sleep-promoting amount of doxylamine is from 2 to 50 milligrams.

15. A method as claimed in claim 14, wherein said sleep-promoting amount of doxylamine is from 5 to 25 milligrams.

16. A method as claimed in claim 15, wherein said sleep-promoting amount of doxylamine is from 10 to 20 milligrams.

17. A method as claimed in claim 12, wherein said anionic surfactant amount is at least 0.25 wt. %.

18. A method as claimed in claim 17, wherein said anionic surfactant amount is at least 0.5 wt. %.

19. A method as claimed in claim 18, wherein said anionic surfactant amount is at least 1.0 wt. %.

20. A method as claimed in claim 12, wherein said anionic surfactant is a salt of a long chain hydrocarbon with a functional group selected from the group consisting of carboxylates, sulfonates and mixtures thereof.

21. A method as claimed in claim 12, wherein said anionic surfactant is a salt of a long chain hydrocarbon with a sulfate functional group.

22. A method as claimed in claim 21, wherein said anionic surfactant is sodium lauryl sulfate.

23. A method as claimed in claim 12, wherein said mammal is a human.

24. An intranasal dosage unit for promoting sleep in a mammal, comprising:

an aqueous buffered solution having a pH greater than 7.5, a sleep-promoting amount of doxylamine succinate and an effective amount of an anionic surfactant, wherein said pH and said anionic surfactant amount are at a level that provides a peak blood plasma concentration of doxylamine within 30 minutes of administering said dosage unit to the nasal mucosa of said mammal.

25. An intranasal dosage unit as claimed in claim 24, wherein said pH and said anionic surfactant amount are at a level that provides a peak blood plasma concentration of doxylamine within 20 minutes of administering said dosage unit to the nasal mucosa of said mammal.

26. An intranasal dosage unit as claimed in claim 25, wherein said pH and said anionic surfactant amount are at a level that provides a peak blood plasma concentration of doxylamine within 10 minutes of administering said dosage unit to the nasal mucosa of said mammal.

27. An intranasal dosage unit as claimed in claim 24, wherein said anionic surfactant is a salt of a long chain hydrocarbon with sulfate functional group.

28. An intranasal dosage unit as claimed in claim 27, wherein said anionic surfactant is sodium lauryl sulfate.

29. An intranasal dosage unit as claimed in claim 28, wherein said pH is at least 8.0.

30. An intranasal dosage unit as claimed in claim 24, wherein said mammal is a human.

* * * * *